United States Patent [19]

Kao et al.

[11] Patent Number: 5,231,978
[45] Date of Patent: Aug. 3, 1993

[54] NON-POWERED, PORTABLE APPARATUS FOR CLEANING THE MOUTH

[76] Inventors: Tony Kao, 2nd Fl., 14, Sublane 1, Lane 94, Ta Chih Street; C. S. Yang, 6th Fl., 41, Lane 228, Ho Ping East Road, Sec. 3, both of Taipei, Taiwan

[21] Appl. No.: 926,646
[22] Filed: Aug. 10, 1992
[51] Int. Cl.⁵ .................................. A61G 17/02
[52] U.S. Cl. ........................................ 128/66
[58] Field of Search ............................ 128/66; 433/80

[56] References Cited

U.S. PATENT DOCUMENTS

| 3,386,439 | 6/1968 | Harper | 128/66 |
| 3,499,440 | 3/1970 | Gibbs | 128/66 |
| 3,973,558 | 8/1976 | Stouffer et al. | 128/66 |
| 4,135,501 | 1/1979 | Leunissan | 128/66 |
| 4,941,459 | 7/1990 | Mathur | 433/88 |

Primary Examiner—John J. Wilson
Attorney, Agent, or Firm—Jones, Tullar & Cooper

[57] ABSTRACT

An apparatus for cleaning the mouth includes chuck unit fastened to the outlet pipe of a water tap and locked in place by a locknut, a spray gun connected to the chuck unit by a spiral water tube, wherein the spray gun has a control valve controlled to eject a stream of water for cleaning the cavity of the mouth. A toothbrush may be attached to the handle of the spray gun in place of the nozzle thereof for cleaning the teeth. The toothbrush has water outlets on the brush head thereof through which water is ejected for cleaning the gaps in the teeth.

9 Claims, 5 Drawing Sheets

NON-POWERED, PORTABLE APPARATUS FOR CLEANING THE MOUTH

BACKGROUND OF THE INVENTION

The present invention relates to a non-powered, portable apparatus for cleaning the teeth and the cavity of the mouth, which is easy to operate and does not consume any electric power.

In order to keep the teeth and the cavity of the mouth clean, the teeth and the cavity of the mouth must be regularly washed. A variety of automatic apparatus are known and widely in use for cleaning the teeth and the cavity of the mouth. These automatic apparatus are commonly heavy and expensive to manufacture, and they require a specific electric working voltage for operation. They may produce high noises when operated. Furthermore, most of these automatic apparatus have no mechanism for regulating the flow rate of water. Although some of these automatic apparatus may have a mechanism for regulating the flow rate of water, the mechanism is commonly difficult to control.

SUMMARY OF THE INVENTION

The present invention has been accomplished under the aforesaid circumstances in view. It is therefore an object of the present invention to provide an apparatus for cleaning the mouth which is portable and convenient for use by an individual while one travels. It is another object of the present invention to provide an apparatus for cleaning the mouth which operates without the consumption of electric power. It is still another object of the present invention to provide an apparatus for cleaning the mouth which is inexpensive to manufacture and easy to install. It is still another object of the present invention to provide an apparatus for cleaning the mouth which can be alternatively attached with a nozzle or a toothbrush for cleaning the cavity and the teeth of the mouth. According to the present invention, the apparatus is comprised of a chuck unit, a spray gun, and a spiral water tube. The chuck unit is for fastening to the outlet pipe of a water tap conveniently. The spray gun comprises a nozzle tube coupled to a handhold and controlled by a control valve. Through a swivel knob, the control valve is controlled to regulate the flow rate of water passing through. A toothbrush may be attached to the handhold in place of the nozzle tube for cleaning the teeth of the mouth. The toothbrush has water outlet holes on the brush head thereof, through which water is ejected for cleaning the teeth and the gaps in the teeth.

DETAILED DESCRIPTION OF THE PREFERRED EMBODIMENT

Figure 1:
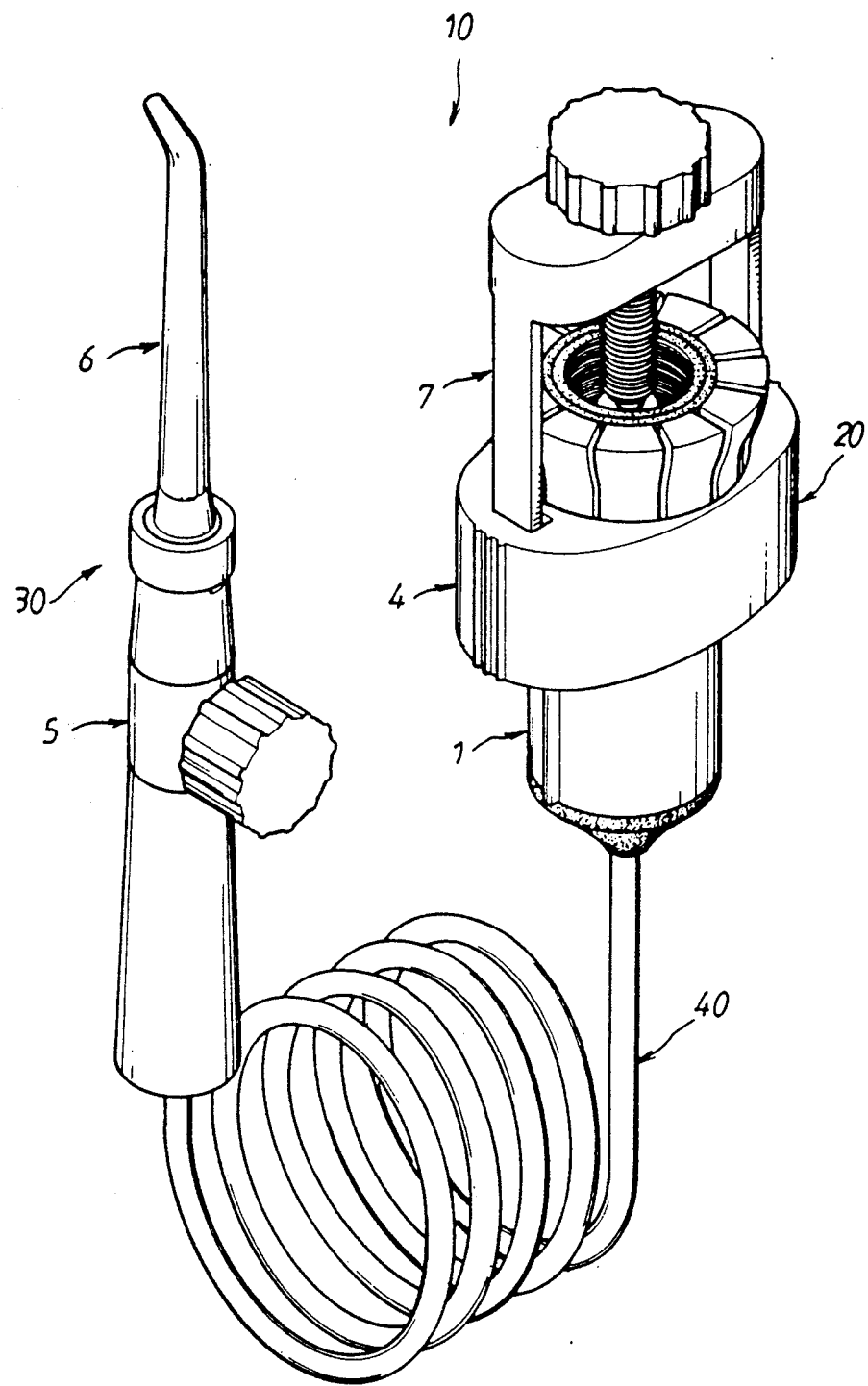
FIG. 1 is a perspective view of a non-powered, portable apparatus for cleaning the mouth embodying the present invention.

Referring to FIG. 1, the apparatus 10 is generally comprised of a chuck unit 20, a spray gun 30, and a water tube 40 connected between the chuck 20 and the spray gun 30.

Figure 2:
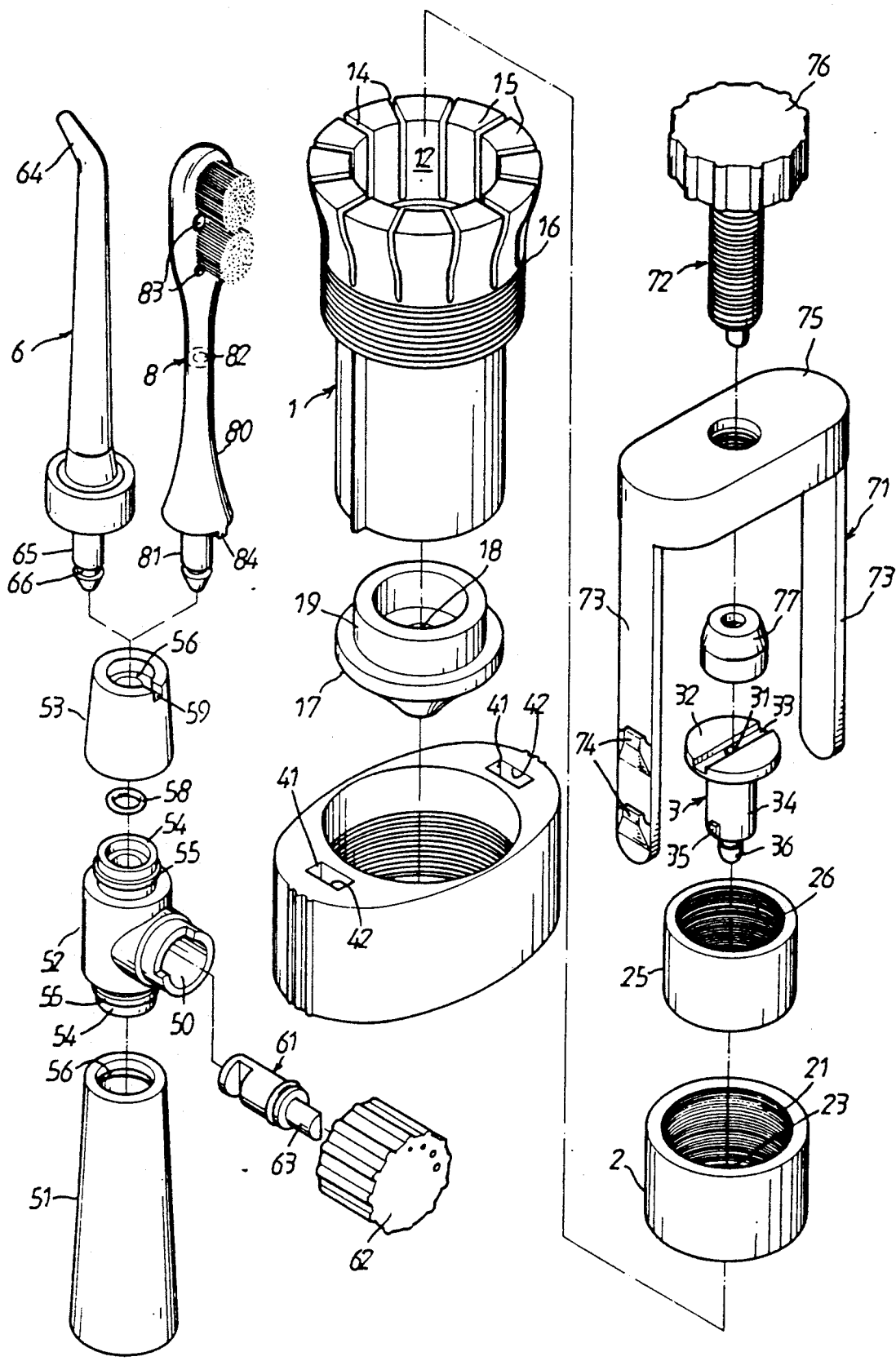
FIG. 2 is an exploded view view of the apparatus of FIG. 1.

Referring to FIG. 2, the chuck unit 20 comprises a cylindrical chuck 1 defining a mounting chamber 12 on the inside above a transverse division wall 11 thereof to hold a rubber cup 2 for mounting on the outlet of a water tap. The elastic material property of the rubber cup 2 allows the chuck unit 20 to be fastened to any of a variety of water tapers. A socket ring 25 is tightly fitted into the rubber cup 2 for mounting on a water tap of smaller size. The rubber cup 2 and the socket 25 have each an anti-skid thread 21 or 26 over the respective inside surface, which greatly increases the frictional resistance against the water tap on which the rubber cup 2 or the socket 25 is mounted. The rubber cup 2 may be separately used for mounting on a water tap of relatively bigger diameter. The socket 25 must be fitted into the rubber cup 2 for mounting on a water tap of relatively smaller diameter.

Figure 3:
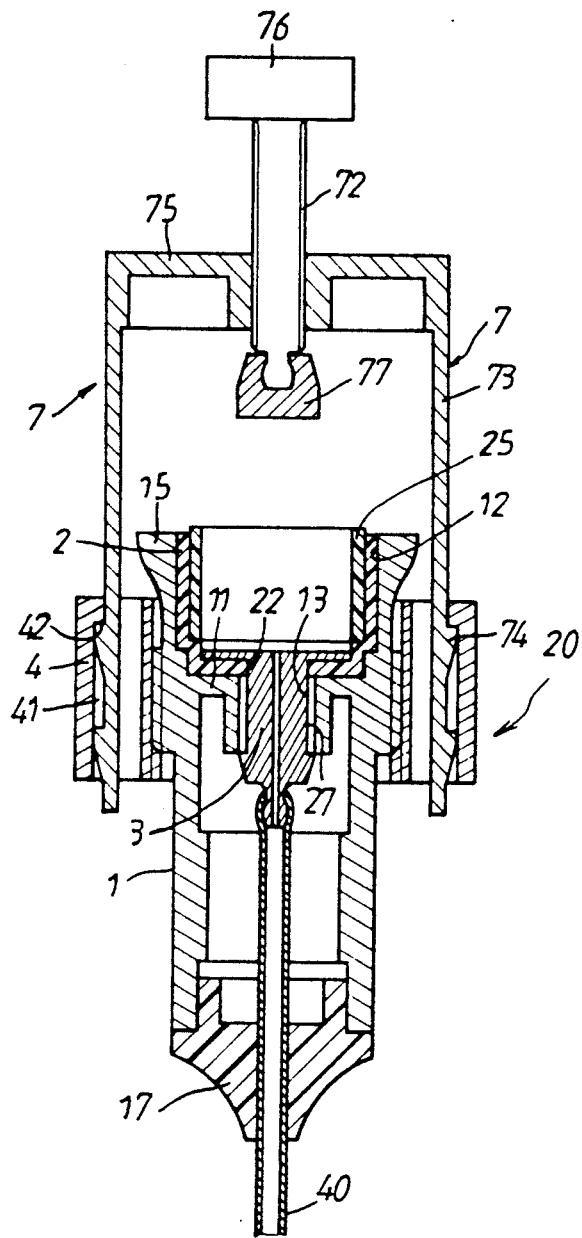
FIG. 3 is a sectional view of the chuck unit of the apparatus of FIG. 1 taken in longitudinal direction.

Referring to FIG. 3 and seeing FIG. 2 again, the transverse division wall 11 and the rubber cup 2 have each a center hole 13 or 22 longitudinally aligned for inserting a water tube connector 3. The water tube connector 3 is made in the shape of a stepped bolt having a round head 32 received in a chamber 23 defined inside the rubber cup 2, a transverse groove 33 through the top edge of the round head 32 for driving a flat screw driver, an axle body 34 vertically extended downward from the the round head 32 and inserted through the center hole 22 on the socket 25, two opposite blocks 35 symmetrically raised from the axle body 34 inserted through two opposite grooves 27 on the center hole 13 and rotated through a certain angle to become locked below the division wall 11, a bottom rod 36 vertically extended downward from the axle body 34 for connecting the water tube 40, and a through hole 31 through the central axis thereof (longitudinally pierced through the round head 32, the axle body 34 and the bottom rod 36) for passing water. The water tube 40 is made from a flexible material arranged in the shape of a coil, and therefore it can be conveniently extended to fit different situations.

Referring to FIGS. 2 and 3 again, the mounting chamber 12 in made in the shape of a taper hole gradually reducing toward the bottom. The top peripheral wall of the cylindrical chuck 1 is divided by a plurality of longitudinal grooves 14 into a plurality of pawls 15 around the mounting chamber 12. The cylindrical chuck 1 further comprises an outer thread 16 below the pawls 15 onto which a locknut 4 is threaded to binding up the pawls 15. Therefore, by means of rotating the locknut 4 inwards or outwards on the outer thread 16, the pawls 15 are squeezed or released for chucking different water taps. As illustrated in FIGS. 2 and 3, the bottom end of the cylindrical chuck 1 is blocked up by a rubber cap 17. The rubber cap 17 has a guide hole 18 through the longitudinal axis thereof, through which the water tube 40 is inserted, and a connecting end 19 tightly fitted into the bottom opening (not shown) on the cylindrical chuck 1.

Figure 4:
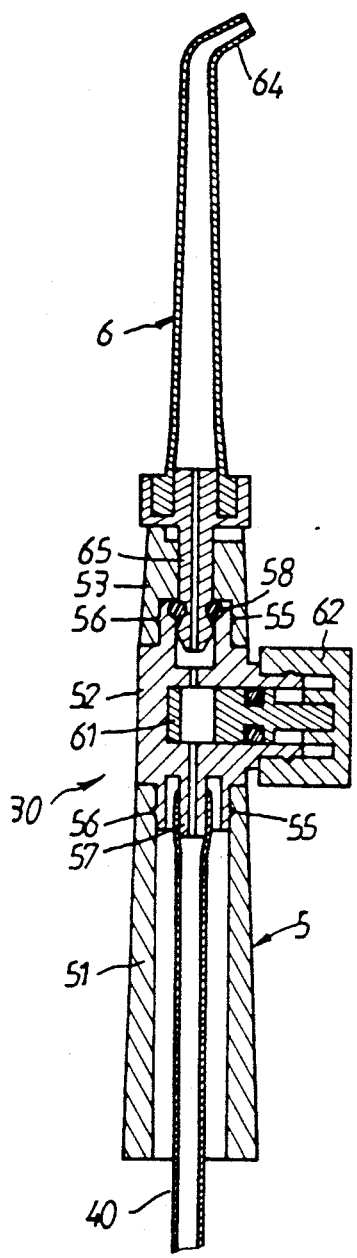
FIG. 4 is a sectional view of the spray gun of the apparatus of FIG. 1 taken in longitudinal direction.

Referring to FIG. 4 and seeing FIG. 2 again, the spray gun 30 is comprised of a handle 5 and a nozzle 6. The handle 5 is consisted of a handhold 51, a valve seat 52 and a nozzle connector 53. The handhold 51 is made in a hollow structure for passing the water tube 40. The valve seat 52 has two annular flanges 55 around two relatively smaller opposite ends 54 thereof respectively engaged in a respective inside annular groove 56 on the handhold 51 or the nozzle connector 53, and therefore the nozzle connector 53 is connected to the handhold 51 by the valve seat 52. Of course, a screw joint or any of a variety of other connecting methods may be employed to connect the handhold 51, the valve seat 52 and the nozzle connector 53 together. The valve seat 52 has a connector 57 on the inside, which receives the water tube 40. An O-ring 58 is fastened inside the top end of the valve seat 52 so seal the gap between the nozzle 6. The nozzle 6 has a top end formed into a nozzle tip 64 and a bottom end formed into a plug tube 65. The plug tube 65 of the nozzle 6 has neck 66 adjacent to the bottom end thereof. When assembled, the plug tube 65 is inserted through the nozzle connector 53 into a hole (not shown) on the valve seat 52, and the O-ring 58 is mounted around the neck 66 to seal the gap between the nozzle connector 53 and the nozzle 6. The valve seat 52 has a valve chamber 50, which receives a valve rod 61. The valve rod 61 has one end 63 coupled to a swivel knob 62. Rotating the swivel knob 62 causes the valve chamber 50 to be blocked up or opened.

Figure 6:
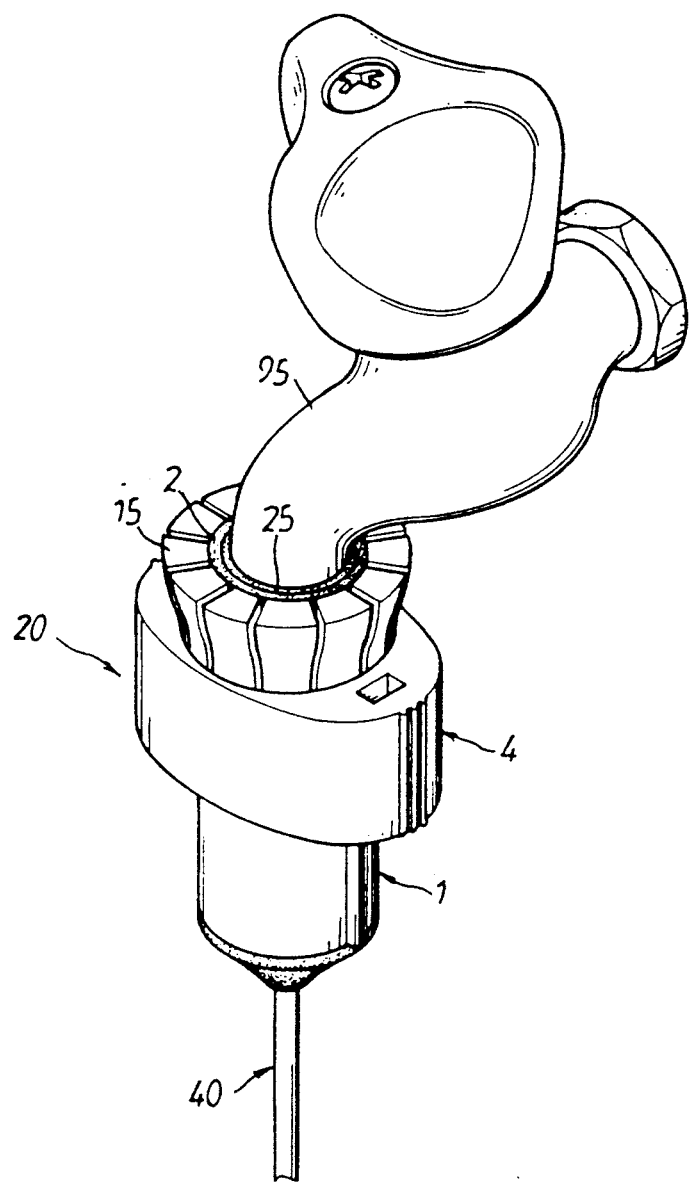
FIG. 6 illustrates another installed example according to the present invention.

Referring to FIG. 6, the rubber cup 2 or the socket 25 is sleeved on the outlet pipe 95 of a water tap and locked in place by screwing up the locknut 4 tightly, and therefore the chuck unit 20 is fastened to the water tap.

Figure 5:
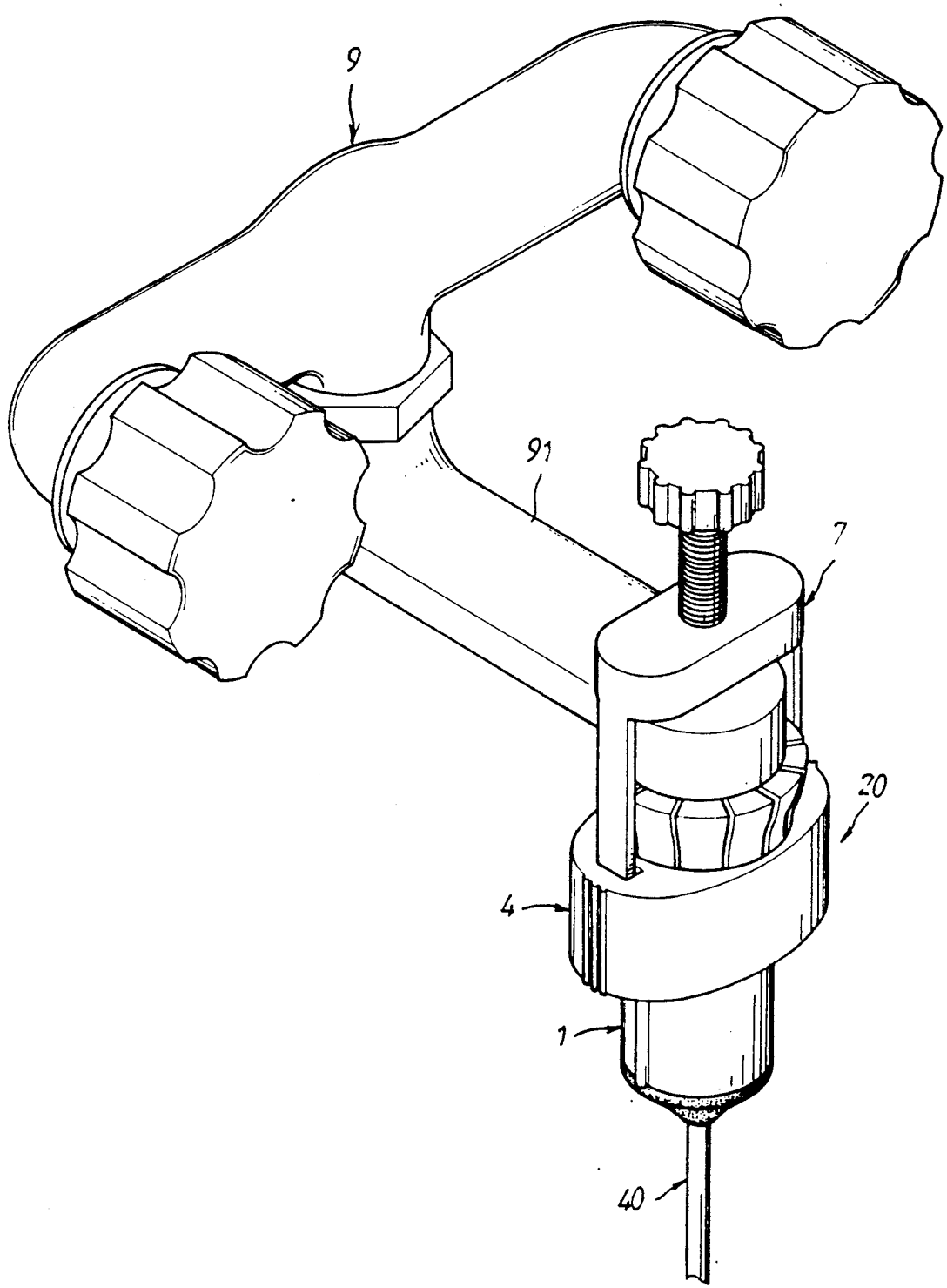
FIG. 5 illustrates an installed example according to the present invention.

Referring to FIG. 5, a mounting device 7 may be used for mounting the chuck unit 20 on a water tap 9 having a transverse outlet pipe 91. As illustrated in FIGS. 2 and 5, the mounting device 7 is comprised of a mounting frame 71 and a tightening up screw 72. The tightening up screw 72 is threaded into a screw hole 78 on the transverse top head 75 of the mounting frame 71. The mounting frame 71 comprises two legs 73 vertically extended downward from the two opposite ends of the transverse top head 75 thereof. The legs 73 of the mounting frame 71 have each a plurality of resilient projections 74 on the outside. By inserting the legs 73 into respective holes 41 on the locknut 4, the resilient projections 74 are hooked up with respective inside flanges 72 inside the holes 41, and therefore the locknut 4 becomes connected to the mounting frame 71. The tightening up screw 72 has a top end formed into a hand wheel 76 for rotating by the hand, and a bottom end coupled with a rubber cone 77 stopped against the outlet pipe 91 of the water tap 9 onto which the mounting frame 7 is mounted.

The operation of the present invention is quite simple and outlined hereinafter. After the chuck unit 20 has been fastened to a water tap, the water tap is turned on, and the handle 5 is held with one hand. Use the thumb of the same hand to rotate the swivel knob 62, and therefore the flow rate of water is properly regulated. As the flow of water from the water tap passed through the nozzle 6, the pressure of water is greatly increased (because the water passage way is greatly reduced relative to the water passage way of the outlet pipe of the water tap), and therefore a stream of water is continuously ejected out of the nozzle tip 64 for cleaning the teeth and the cavity of the mouth.

Referring to FIG. 2 again, a toothbrush 8 may be used in place of the nozzle 6. The toothbrush 8 comprises a plug tube 81 on the bottom end thereof inserted through the nozzle connector 53 and connected to the valve seat 52 on the inside. The structure of the plug tube 81 is similar to the plug tube 65 on the nozzle 6, and therefore it can be conveniently connected to the valve seat 52 on the inside. The toothbrush 8 has a water passage hole 82 through the brush handle 80 thereof. The water passage hole 82 has one end connected to the valve chamber 50 and an opposite end connected to a plurality of outlet holes 83 on the brush head around the bristles thereof. The brush handle 80 of the toothbrush 8 has a tongue 84 on the bottom edge thereof inserted in a groove 59 on the top edge of the nozzle connector 53, and therefore the toothbrush 8 is prohibited from a rotary motion.

What is claimed is:

1. An apparatus for cleaning the mouth comprising:
   a hollow cylindrical chuck having a mounting chamber surrounded by a plurality of pawls and an outer thread below said pawls;
   a rubber cup fitted into said mounting chamber for fastening to the outlet pipe of a water tap;
   a water tube connector having one end supported on said rubber cup and an opposite end inserted through a hole on said rubber cup for connecting a water tube, said water tube connector having a water passage hole through the longitudinal axis thereof;
   a locknut threaded onto the outer thread of said cylindrical chuck to bind up said pawls causing said rubber cup to be tightly fastened to the outlet pipe of the water tap onto which it is mounted;
   a hollow handle having a control valve controlled to regulate the flow of water passing through;
   a nozzle tube having one end coupled to said hollow handle and an opposite end terminated into a nozzle tip; and
   a water tube connected between said water tube connector and said handle for guiding a flow of water from a water tap to said nozzle tube for cleaning the teeth and the cavity of the mouth.

2. The apparatus of claim 1 which further comprises a mounting device for securing said cylindrical chuck to the outlet pipe of a water tap, said mounting device comprising an invertedly U-shaped mounting frame having two legs inserted in holes on said locknut and locked therein through a hooked joint, and a tightening up screw threaded through a screw hole on a transverse top head of said mounting frame and tightly stopped against the outlet pipe of the water tap.

3. The apparatus of claim 2 wherein said tightening up screw has a bottom end coupled with a rubber cone.

4. The apparatus of claim 1 wherein said water tube is made from a flexible material arranged in the shape of a coil.

5. The apparatus of claim 1 wherein a socket is tightly fitted into said rubber cup for mounting on the outlet pipe of a water tap.

6. The apparatus of claim 5 wherein said rubber cup and said socket have each an anti-skid thread over the respective inside surface.

7. The apparatus of claim 1 wherein a toothbrush may be alternately attached to said hollow handle, said toothbrush having a water passage hole through a brush handle thereof, the water passage hole of said toothbrush having one end connected to said hollow handle and an opposite terminated into a plurality of water outlet holes on a brush head thereof.

8. The apparatus of claim 1 wherein said cylindrical chuck has a bottom end sealed by an end cap, said end cap having a guide hole for passing said water tube.

9. The apparatus of claim 1 wherein said water tube connecting has two opposite blocks symmetrically raised from an axle body thereof, said blocks being inserted through two opposite grooves on said cylindrical chuck and locked below a bottom wall on said mounting chamber of said cylindrical chuck through a rotary control.

* * * * *